United States Patent
Yates et al.

(10) Patent No.: US 7,018,816 B2
(45) Date of Patent: Mar. 28, 2006

(54) REAL-TIME POLYMERASE CHAIN REACTION-BASED GENOTYPING ASSAY FOR SINGLE NUCLEOTIDE POLYMORPHISM

(75) Inventors: Charles R. Yates, Memphis, TN (US); Duane Miller, Memphis, TN (US); Dick Gourley, Memphis, TN (US); Pengfei Song, Memphis, TN (US)

(73) Assignee: The University of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 10/809,757

(22) Filed: Mar. 25, 2004

(65) Prior Publication Data

US 2004/0191822 A1 Sep. 30, 2004

Related U.S. Application Data

(60) Provisional application No. 60/457,512, filed on Mar. 25, 2003, now abandoned.

(51) Int. Cl.
*C12P 19/34* (2006.01)
(52) U.S. Cl. .............. 435/91.2; 435/6; 536/24.31; 536/24.3; 536/23.1
(58) Field of Classification Search ................ 536/23.1, 536/24.3, 24.31; 435/91.2, 6
See application file for complete search history.

(56) References Cited

OTHER PUBLICATIONS

Song et al. (AAPS PharmSci 2002; 4(4) article 29 (http://www.aapspharmsci.org), published Oct. 2, 2002).*
Song et al. (Clinical Pharmacology & Therapeutics, vol. 71, No. 2, Feb. 2002, p. P103, abstract WPIII-100).*
Hoffmeyer et al. (PNAS, vol. 97, No. 7, pp. 3473-3478, Mar. 28, 2000).*
GenBank M14758 (GI: 187468, Dec. 3, 1999).*
Okimoto et al. (Bio Techniques, vol. 21, Jul. 1996), pp. 20,22, 24, 26.*
GenBank AC005068 (GI: 10122135, Oct. 7, 2000).*

* cited by examiner

*Primary Examiner*—Juliet C. Switzer
(74) *Attorney, Agent, or Firm*—Benjamin Aaron Adler

(57) ABSTRACT

The present invention provides fluorescence-based real-time PCR assays for the rapid detection of single nucleotide polymorphisms (SNPs). The genotyping assay can be used to detect SNPs of a number of genes of interest that include, but are not limited to, the human multidrug resistance gene (MDR1) single nucleotide polymorphisms C3435T and G2677T, and cytochrome P-450 3A5 single nucleotide polymorphisms CYP3A5*3 (A22893G) and CYP3A5*6 (G30597A).

4 Claims, 5 Drawing Sheets

REAL-TIME POLYMERASE CHAIN REACTION-BASED GENOTYPING ASSAY FOR SINGLE NUCLEOTIDE POLYMORPHISM

CROSS-REFERENCE TO RELATED APPLICATION

This application claims benefit of provisional patent application U.S. Ser. No. 60/457,512, filed Mar. 25, 2003, now abandoned.

BACKGROUND OF THE INVENTION

1. Field of the Invention

The present invention relates generally to the field of single nucleotide polymorphism genotyping. More specifically, the present invention provides a real-time polymerase chain reaction-based genotyping assay for the detection of single nucleotide polymorphisms.

2. Description of the Related Art

P-glycoprotein (P-gp), a member of the large adenosine triphosphate-binding (ATP-binding) cassette superfamily of transport proteins also called traffic ATPases, is the product of the human multidrug resistance gene (MDR1). P-glycoprotein is highly expressed on the apical (luminal) surface of organs that have excretory functions, such as the bile canalicular membrane of hepatocytes and the renal proximal tubule. Moreover, P-glycoprotein is significantly expressed on the luminal surface of tissues that serve as barriers, such as the brush border of the small intestine and the capillary endothelial cells of the blood-brain barrier.

Tissue distribution suggests that P-glycoprotein protects the body from toxic xenobiotics by secreting them into the bile, urine, and intestinal lumen and by reducing their accumulation in the brain and testes. As a result, interindividual variability in the disposition of numerous drugs has been ascribed to differences in P-gp expression. It has been reported that intestinal P-glycoprotein expression accounted for approximately 30% of interindividual variability in the maximal plasma concentration after oral administration of cyclosporine.

A novel P-glycoprotein aberrant allele, MDR1*2, linked to 2 synonymous single nucleotide polymorphisms (SNPs) (C1236T in exon 12 and C3435T in exon 26) and a non-synonymous single nucleotide polymorphism in exon 21 (G2677T, Ala893Ser) was recently described (Kim et al., 2001). The single nucleotide polymorphisms found on exons 12, 21, and 26 are not strictly allelic; however, they exhibit strong linkage disequilibrium and account for a majority of the described haplotypes (Kim et al., 2001; Tang et al., 2002). MDR1*2 was found to be associated with altered fexofenadine disposition. Individuals carrying 2 wild type alleles (*1/*1) had a 40% greater fexofenadine systemic exposure after oral administration compared with individuals heterozygous or homozygous for MDR1*2. Reduced fexofenadine systemic exposure in carriers of the MDR1*2 allele potentially results in reduced therapeutic benefit after oral administration of fexofenadine.

Kim et al. (2001) reported significant ethnic differences in MDR1*2 allelic frequency, with 62% and 13% of European Americans and African Americans, respectively, carrying at least one MDR1*2 allele. Thus, polymorphic MDR1 expression may contribute to interracial variability in drug disposition. Unfortunately, attempts to determine the association between polymorphic P-glycoprotein expression and drug disposition have yielded equivocal results.

To facilitate clarification of the significance of commonly occurring MDR1 single nucleotide polymorphisms and their ethnic frequency on drug disposition, a rapid and robust polymerase chain reaction-based (PCR-based) screening method for the single nucleotide polymorphisms C3435T and G2677T would be highly desirable. The present invention fulfills this longstanding need and desire in the art.

SUMMARY OF THE INVENTION

The present invention provides a real-time polymerase chain reaction (PCR)-based method to detect single nucleotide polymorphisms. Discrimination between wild type and mutant alleles was achieved using PCR amplification of specific alleles modified to prevent non-Watson Crick base pairing (Okimoto & Dodgson, 1996; Sommer et al., 1992; Bottema et al., 1993; Newton et al., 1989). Two key nucleotide mismatches are required for alleleic discrimination. The first nucleotide difference between primers used to discriminate between wild type and mutant alleles was located at the 3' terminal base. However, a single base pair difference at the 3' end of the primer is insufficient, in most cases, to achieve allelic discrimination. An additional internal nucleotide mismatch (typically within 5 base pairs of the 3' end) is required for specific amplification of either the wild-type or mutant allele. Thus, a second nucleotide mismatch located three bases from the 3' end for both the wild-type and mutant-specific primers was included to generate an internal primer/template mismatch that prevents amplification of the nonmatching primer.

In one embodiment, the present invention provides a genotyping assay to detect MDR1 (human multidrug resistance gene) single nucleotide polymorphisms (SNPs) C3435T and G2677T. C3435T and G2677T are linked to MDR1*2, which is associated with enhanced efflux activity in vitro and in vivo. PCR reactions for genotyping C3435T and G2677T using allele-specific primers were conducted in separate tubes. PCR amplification was monitored by Smart Cycler (Cepheid, Sunnyvale, Calif.) using SYBR™ Green I, a non-specific double stranded DNA intercalating fluorescent dye. PCR growth curves exceeding the threshold cycle were considered positive. Fluorescence melt-curve analysis was used to corroborate results from PCR growth curves.

Using PCR growth curves, the assay disclosed herein accurately determined hetero- and homozygosity for C3435T and G2677T. Genotype assignments based on PCR growth curve, melt-curve analysis, agarose gel electrophoresis, and direct DNA sequencing results of PCR products were in perfect agreement. Thus, the present invention provides a rapid MDR1 genotyping method that can be used to assess the contribution of MDR1*2 to pharmacokinetic and pharmacodynamic variability of P-gp substrates.

In another embodiment, the above described real-time PCR-based method was used to detect cytochrome P-450 3A5 (CYP3A5) single nucleotide polymorphisms CYP3A5*3 (A22893G) and CYP3A5*6 (G30597A).

Other and further aspects, features, and advantages of the present invention will be apparent from the following description of the presently preferred embodiments of the invention. These embodiments are given for the purpose of disclosure.

DETAILED DESCRIPTION OF THE INVENTION

Figure 1A:
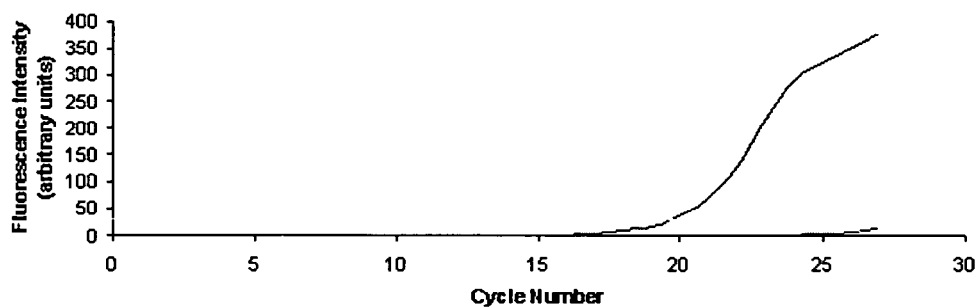
FIGS. 1A–D: MDR1 C3435T allelic discrimination by real-time analysis using the Smart Cycler. Plot of fluorescence versus cycle number using human genomic DNA obtained from individuals with CC (FIG. 1A), TT (FIG. 1B), or CT (FIG. 1C) genotypes and nontemplate control (FIG. 1D). Interrogation for the presence of either the C or T allele was conducted in physically separate tubes using the common reverse primer 3435R coupled with either the wild type specific primer 3435W (-♦-, blue) or the mutant-specific primer 3435M (-•-, pink). PCR growth curves that exceed the threshold fluorescence indicate specific PCR product formation.

Fluorescence-based single nucleotide polymorphism detection assays offer several important advantages over traditional PCR approaches used to determine genotype (e.g. sequencing of PCR products and restriction fragment length polymorphism, RFLP). First, RFLP can in some instances result in significant false positive rates as a result of incomplete restriction enzyme digestion or the presence of other mutations close to the mutation of interest. Second, fluorescence-based genotyping assays are more amenable to high-throughput screening, as they do not require extensive post-amplification manipulation.

Commonly used fluorescence-based PCR techniques for single nucleotide polymorphism detection include the use of either the nonspecific DNA intercalating dye SYBR™ Green I or an allele-specific fluorogenic probe (i.e. Taqman). In many instances, the use of SYBR™ Green I is more cost-effective when applied to haplotype analysis of genes with multiple allelic variants since it does not require the synthesis of numerous allele-specific fluorogenic probes.

In the present invention, the use of allele-specific primers containing an additional internal mismatch obviates the need for extensive optimization of PCR amplification conditions associated with traditional PCR amplification of specific alleles. The inventors have successfully applied the approach described here to genotype 11 other single nucleotide polymorphisms using, in most instances, identical PCR amplification conditions.

Current methods for genotyping MDR1 or CYP3A5 include PCR amplification followed by sequencing and fluorogenic probe-based PCR assays. The simple, rapid, inexpensive, reproducible, and reliable real-time PCR genotyping methods presented here constitute a significant improvement over current techniques. Using this approach, genotyping results can be obtained within 2 hours of whole blood or tissue procurement. Importantly, these techniques are also applicable in laboratories lacking access to real-time PCR equipment since allelic discrimination can be determined using traditional PCR and agarose gel electrophoresis.

Thus, the present invention is directed to a method of genotyping MDR1 single nucleotide polymorphism C3435T, comprising the step of amplifying DNA samples with primers SEQ ID NOs: 1 and 3 or SEQ ID NOs: 2 and 3. The presence of DNA products amplified by primers SEQ ID NOs: 2 and 3 would indicate the individual has the genotype C3435T. In general, the amplified DNA products can be identified by real-time fluorescence-based analysis, melt curve analysis or gel electrophoresis. In the case of gel electrophoresis, the presence of a 134 base pairs product corresponds to genotype C3435T.

In another embodiment, there is provided a method of genotyping MDR1 single nucleotide polymorphism G2677T, comprising the step of amplifying DNA samples with primers SEQ ID NOs: 4 and 6 or SEQ ID NOs: 5 and 6. The presence of DNA products amplified by primers SEQ ID NOs: 5 and 6 would indicate the individual has the genotype G2677T. In general, the amplified DNA products can be identified by real-time fluorescence-based analysis, melt curve analysis or gel electrophoresis. In the case of gel electrophoresis, the presence of a 216 base pairs product corresponds to genotype G2677T.

In yet another embodiment, there is provided a method of genotyping human cytochrome P-450 3A5 single nucleotide polymorphism CYP3A5*3, comprising the step of amplifying DNA samples with primers SEQ ID NOs: 11 and 13 or SEQ ID NOs: 12 and 13. The presence of DNA products amplified by primers SEQ ID NOs: 12 and 13 would indicate the individual has the genotype CYP3A5*3. In general, the amplified DNA products can be identified by real-time fluorescence-based analysis, melt curve analysis or gel electrophoresis. In the case of gel electrophoresis, the presence of a 238 base pairs product corresponds to genotype CYP3A5*3.

In still yet another embodiment, there is provided a method of genotyping human cytochrome P-450 3A5 single nucleotide polymorphism CYP3A5*6, comprising the step of amplifying DNA samples with primers SEQ ID NOs: 14 and 16 or SEQ ID NOs: 15 and 16. The presence of DNA products amplified by primers SEQ ID NOs: 15 and 16 would indicate the individual has the genotype CYP3A5*6. In general, the amplified DNA products can be identified by real-time fluorescence-based analysis, melt curve analysis or gel electrophoresis. In the case of gel electrophoresis, the presence of a 273 base pairs product corresponds to genotype CYP3A5*6.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

MDR1 Single Nucleotide Polymorphisms Genotyping

The present example describes a real-time PCR assays for the rapid detection of the MDR1 single nucleotide polymorphisms C3435T and G2677T. These methods can be readily applied to investigate the effect of MDR1 polymorphic expression on pharmacokinetic and pharmacodynamic variability of P-gp substrates.

EXAMPLE 2

Primer Design

PCR primers are listed in Table 1. Oligonucleotide primers were designed based on the published MDR1 sequence (Genbank #AC005068) using the online program Primer3. Hairpin structures and primer-dimers were predicted with Oligo Toolkit™. The primers were synthesized by Integrated DNA Technologies (Coralville, Iowa). Expected amplicon lengths were 216 base pairs (bp) and 134 bp for G2677T and C3435T, respectively. Discrimination between wild type and mutant alleles was achieved using PCR amplification of specific alleles modified to prevent non-Watson Crick base pairing (Okimoto & Dodgson, 1996; Sommer et al., 1992; Bottema et al., 1993; Newton et al., 1989). Briefly, the first nucleotide difference (C or T) between sense primers (3435W and 3435M) used to discriminate between wild type and mutant 3435 alleles is located at the 3' terminal base. The second primer base change (A to G) located 3 bases from the 3' end generates an internal primer/template mismatch, and this prevents amplification of the nonmatching primer. These changes were made to prevent the generation of possible spurious products, which could otherwise occur by the annealing and extension of the 3435W primer to the first-round product of 3435M. A similar strategy was used to achieve allelic discrimination for G2677T (Table 1).

EXAMPLE 3

Real-Time PCR Amplification

The Smart Cycler (Cepheid, Sunnyvale, Calif.) was used to monitor PCR amplification using SYBR™ Green I (Molecular Probes, Eugene, Orge.), a nonspecific double-stranded DNA intercalating fluorescent dye. Thus, to achieve allelic discrimination between wild type and mutant alleles, two physically separate PCR reactions containing either wild type or mutant-specific primers were performed. All reactions were carried out in a total volume of 25 μL. Reaction conditions were identical for G2677T and C3435T except where noted. Each reaction mixture contained a 1:12,500 dilution of SYBR™ Green I nucleic acid gel stain 10,000× in dimethyl sulfoxide (DMSO) (Molecular Probes); 0.2 mM of DATP, dCTP, dGTP, and dTTP; 200 nM of both forward and reverse primers; 1.0 U of Taq DNA polymerase (Promega, Madison, Wis.); 6% DMSO; and 20 to 120 ng of genomic DNA in 1× PCR buffer (pH 8.3, 10× solution containing 100 mM Tris-HCl, 500 mM KCl, 15 mM MgCl2 and 0.01% gelatin) (Sigma, St. Louis, Mo.). Genomic DNA was obtained from the Human Genetic Cell Repository, sponsored by the National Institute of General Medical Sciences.

The amplification program for both G2677T and C3435T consisted of 1 cycle of 95° C. with 120-second hold followed by 27 cycles of 95° C. with 6-second hold, specified annealing temperature of 62° C. with 15-second hold, and 72° C. with 20-second hold. After amplification, melt analysis was performed by heating the reaction mixture from 60° C. to 95° C. at the rate of 0.2° C./s. A negative control without DNA template was run with every assay to assess the overall specificity. PCR products for sequencing the 2677 locus were generated using the sense primer (5'-AAGATTGCTTTGAGGAATGGT-3', SEQ ID NO:7) and the antisense primer (5'-GCTATAGGTTCCAGGCTTGCT-3', SEQ ID NO:8). PCR products for sequencing the 3435 locus were generated using the sense primer (5'-GAGCCCATCCTGTTGACTG-3', SEQ ID NO:9) and the antisense primer (5'-ACTATAGGCCAGAGAGGCTGC-3', SEQ ID NO:10).

EXAMPLE 4

PCR Product Analysis

The real-time fluorescence signal generated by the non-specific double-stranded DNA binding dye SYBR™ Green I was analyzed using the Smart Cycler software. A threshold cycle (Ct) was determined for each sample using the exponential growth phase and the baseline signal from fluorescence versus cycle number plots. A sample was deemed positive if fluorescence exceeded the threshold. Threshold fluorescence level was automatically set by the Smart Cycler software. Melt curves were transformed to the negative first derivative melt curves ([−dF/dt] vs temperature). In the melt analysis, the negative first derivative peaks, which are characteristic of the PCR product melt temperature, were used to identify specific PCR products. Amplification reactions were routinely checked for the presence of nonspecific products by agarose gel electrophoresis. PCR products were isolated by QIAquick (Qiagen, Valencia, Calif.) after separation by agarose gel electrophoresis and subjected to direct sequencing using the ABI Prism Model 3100 (Applied Biosystems, Foster City, Calif.). Genomic DNA obtained from individuals determined by sequencing to be homo-, hetero-, and nullizygous for the 2677T and 3435T alleles was used for genotyping assay development and validation.

EXAMPLE 5

MDR1 Genotyping Results

Allele-specific primers containing an additional nucleotide mismatch 3 bases from their 3' termini had little effect on specific PCR product yield. However, nonspecific PCR product yield was drastically reduced to undetectable levels. Consequently, PCR conditions were optimized such that the threshold cycle (Ct) was exceeded only when specific amplification occurred (i.e., only in the presence of a primer:template match). FIG. 1A illustrates the results of the MDR1

C3435T allelic discrimination assay using homozygous 3435C genomic DNA amplified with a common primer 3435R and either the wild-type specific primer 3435W or the mutant-specific primer 3435M. When primers 3435R and 3435W were used to amplify homozygous 3435C genomic DNA, the PCR growth curve exceeded the Ct value at approximately 21 cycles (FIG. 1A), and the melt analysis (negative first derivative) yielded a characteristic sharp peak at approximately 84° C. for the product (FIG. 2A).

Figure 1B:
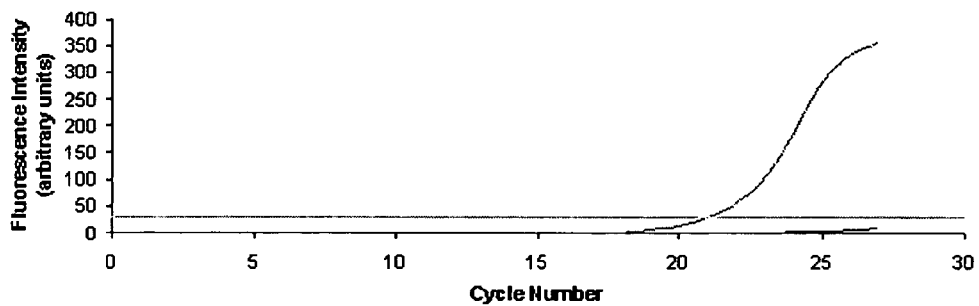
Figure 2A:
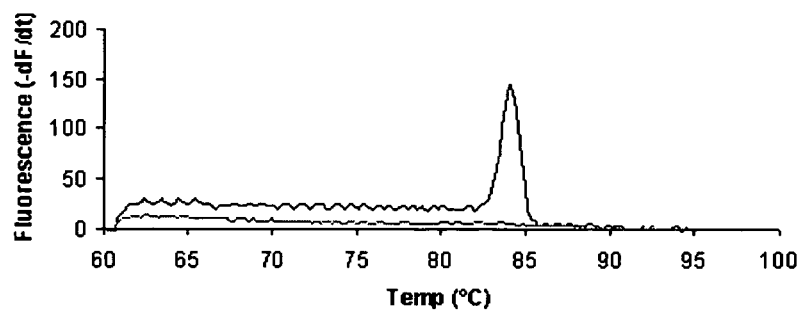
FIGS. 2A–D: Melt curve analysis of PCR products using SYBR™ Green I. Melt curves were converted to melt peaks by plotting the negative first derivative of the fluorescence versus temperature ([−dF/dt]). Plot of [−dF/dt] versus temperature obtained after amplification of CC (FIG. 2A), TT (FIG. 2B), CT (FIG. 2C) genomic DNA and nontemplate control (FIG. 2D) using the common reverse primer 3435R coupled with either the wild type specific primer 3435W or the mutant-specific primer 3435M. The melt temperature ($T_m$=84° C.) was identical for PCR products formed using either the wild type or mutant-specific primers.
Figure 2B:
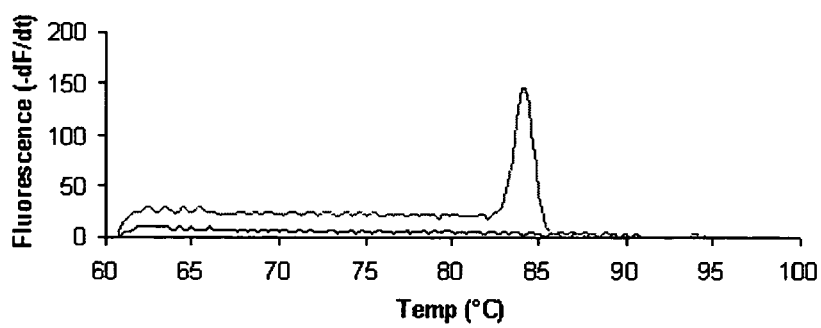
Figure 3:
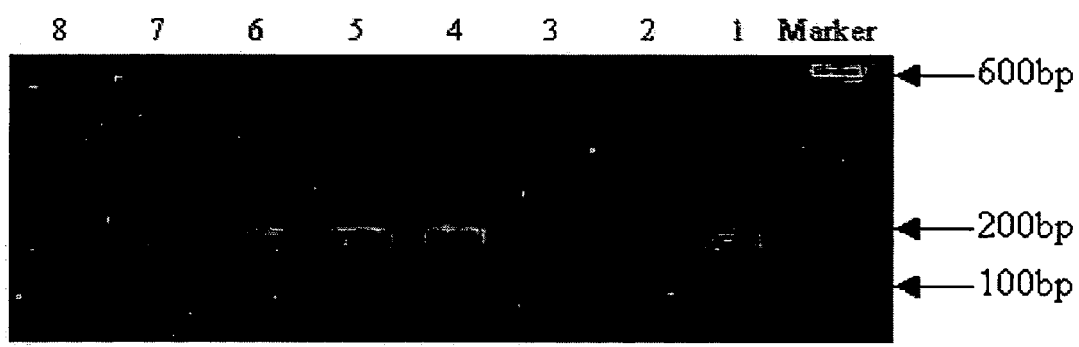
FIG. 3: MDR1 C3435T allelic discrimination by conventional modified allele-specific PCR. An ethidium bromide-stained 2% agarose gel containing PCR fragments (134 bp) was run to confirm real-time PCR results. Odd-numbered lanes contain PCR fragments after amplification with 3435R and 3435W. Even-numbered lanes contain PCR fragments after amplification with 3435R and 3435M. PCR products amplified from genomic DNA with different 3435 genotypes were loaded as follows: CC (lanes 1 and 2), TT (lanes 3 and 4), and CT (lanes 5 and 6). Lanes 7 and 8 represent nontemplate controls. Lane marker contains a 100-bp DNA ladder.

PCR growth curves remained at approximately background fluorescence, and no distinct melt analysis peak was noted when primers 3435R and 3435M were used to amplify homozygous 3435C genomic DNA (FIGS. 1A and 2A). Agarose gel electrophoresis yielded the expected 134-bp fragment when homozygous 3435C DNA was amplified with primers 3435R and 3435W (FIG. 3). However, no bands were visualized after homozygous 3435C DNA was amplified using primers 3435R and 3435M (FIG. 3). Similarly, allelic discrimination was achieved after amplification of homozygous 3435T DNA using primers 3435R, 3435M, and 3435W (FIGS. 1B, 2B, and 3).

Figure 1C:
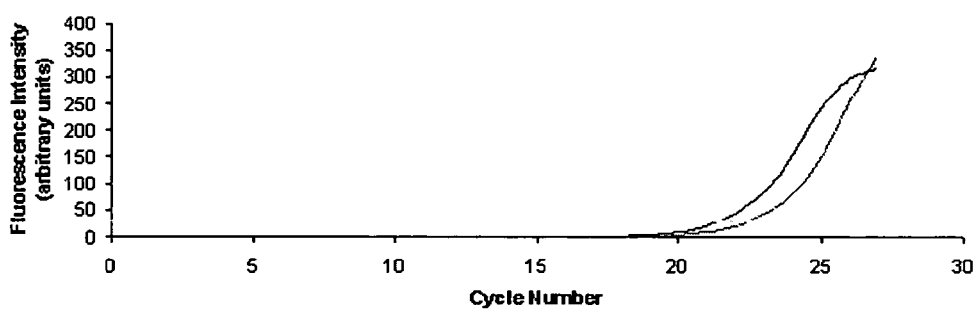
Figure 2C:
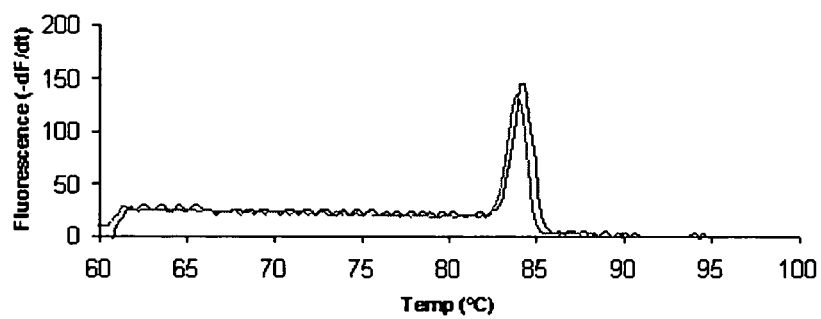

Overlapping PCR growth curves yielding similar Ct values were obtained when CT genomic DNA was amplified using wild-type and mutant-specific primers (FIG. 1C). In addition, a distinct melt analysis peak was present after amplification with both wild-type and mutant-specific primers (FIG. 2C). Results from real-time PCR corroborate conventional PCR results (FIG. 3) and accurately predict the presence of both wild-type and mutant 3435 alleles in the heterozygote control.

Figure 1D:
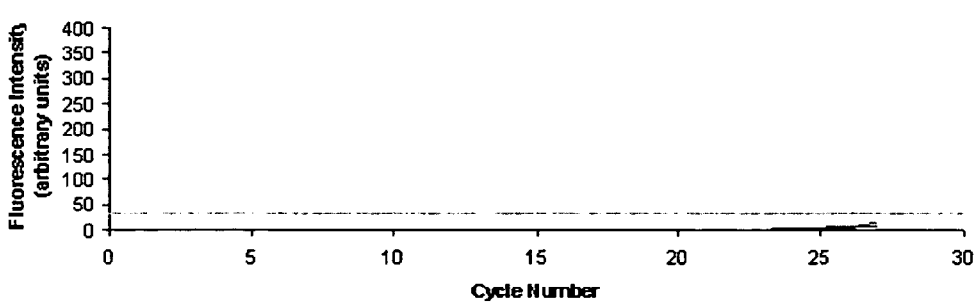
Figure 2D:
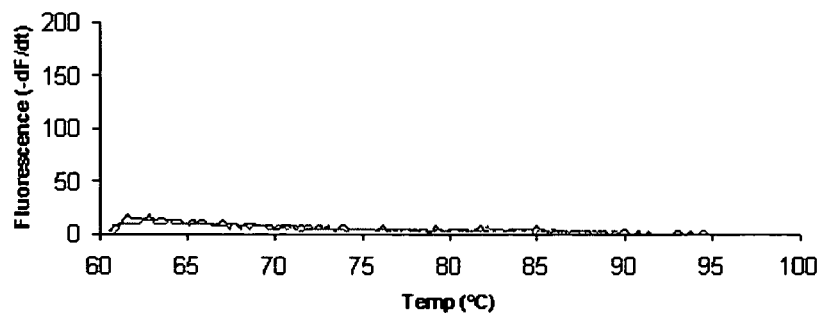

FIGS. 1D and 2D illustrate results from nontemplate control reaction. Results obtained from optimization and application of the G2677T genotyping assay to individuals with GG, GT, and TT genotypes were similar to those reported for C3435T (data not shown). Melt analysis yielded a characteristic sharp peak at approximately 80° C. (Table 1).

The validity of the present methods was verified by testing 20 individuals (10 Caucasians and 10 African Americans) comprising all 3 G2677T and C3435T genotypes. The genotype distribution was in Hardy-Weinberg equilibrium. The allele frequency for 2677T was 0.50 and 0.15 for Caucasians and African Americans, respectively. The allele frequency for 3435T was 0.55 and 0.20 for Caucasians and African Americans. The allele frequencies for 2677T and 3435T were similar to those previously reported for Caucasians and African Americans. Eighteen samples (3 individuals homo-, hetero-, and nullizygous for either 2677T or 3435T) were sequenced. Sequencing results were in perfect agreement with real-time PCR results.

TABLE 1

Primer Sequences For MDR1 Genotyping

| Primer[a] | Sequence[b] | $T_m$[c] |
|---|---|---|
| C3435T | | 84° C. |
| 3435W | 5' 43288 GTGGTGTCACAGGAAGAGGTC 3' 43268 (SEQ ID NO:1) | |
| 3435M | 5' 43288 GTGGTGTCACAGGAAGAGTT 3' 43268 (SEQ ID NO:2) | |
| 3435R | 5' 43155 ACTATAGGCCAGAGAGGCTGC 3' 43175 (SEQ ID NO:3) | |
| G2677T | | 80° C. |
| 2677W | 5' 65221 AGTTTGACTCACCTTCCCTGC 3' 65241 (SEQ ID NO:4) | |
| 2677M | 5' 65221 AGTTTGACTCACCTTCCCTGA 3' 65241 (SEQ ID NO:5) | |
| 2677C | 5' 65436 GCTATAGGTTCCAGGCTTGCT 3' 65416 (SEQ ID NO:6) | |

[a]W indicates wild type specific primer; M, mutant-specific primer; R and C, common primers used in allelic discrimination assays.
[b]Nucleotides shown in bold indicate nucleotides mismatches from published wild type sequence (Genbank #AC005068).
[c]Amplicon melt temperature ($T_m$) obtained from melt curve analysis.

EXAMPLE 6

CYP3A5 Single Nucleotide Polymorphisms Genotyping

The present example describes a real-time PCR assays for the rapid detection of the most prevalent inactivating alleles of the CYP3A5 gene, CYP3A5*3 and CYP3A5*6. These methods can be readily applied to determine the effect of CYP3A5 genotype on inter-individual variability in the pharmacokinetics of CYP3A substrates.

The cytochrome P-450 3A subfamily (CYP3A) is considered the principal isoform of the CYP superfamily. CYP3A is abundantly expressed in the liver and gut epithelium and thus contributes to the high first pass extraction of a large number of orally administered drugs. Establishment of a causal link between highly variable CYP3A activity, exceeding 40% in some populations, and inter-individual variability in the bioavailability of orally administered medications has been the focal point of many studies. However, these research efforts have been limited by a lack of information regarding mechanisms controlling basal expression of CYP3A.

CYP3A4 and CYP3A5 constitute the majority of CYP3A activity in the adult. Polymorphic expression of CYP3A4 and/or CYP3A5 could conceivably contribute to differences in basal CYP3A activity. To date, there have been no polymorphic CYP3A4 alleles linked to clinically significant differences in drug pharmacokinetics.

Recently, Kuehl et al. (2001) described two non-functional allelic variants of the CYP3A5 gene, CYP3A5 *3 and *6. The molecular defect in CYP3A5*3 is a single nucleotide polymorphism (SNP; A22893G) located in intron 3. The molecular defect in CYP3A5*6 is a SNP (G30597A) located in exon 7. More than 50% of African Americans express CYP3A5 compared to 33% of Caucasians. This led Kuehl et al. to speculate that polymorphic CYP3A5 expression may be an important genetic contributor to inter-individual and interracial differences in CYP3A-mediated drug disposition.

EXAMPLE 7

Genomic DNA

Genomic DNA can be extracted from 2 ml whole blood anti-coagulated with trisodium citrate using the QIAmp DNA Blood Midi Kit (Qiagen, Valencia, Calif.) according to manufacturer's instructions. All blood samples were kept at −80° C. until DNA isolation.

EXAMPLE 8

Primer Design

Discrimination between wild-type and mutant alleles was achieved using modified PCR amplification of specific alleles described above. The modification is made to improve amplification specificity by incorporating an additional internal nucleotide mismatch near the 3' termini of the allele-specific primers. PCR primers are listed in Table 2. Oligonucleotide primers were designed based upon the published CYP3A5 sequence (Genbank #AC005020) using the online program Primer3. Oligo Toolkit™ was used to predict hairpin structures and primer-dimers. Primers were synthesized by Integrated DNA Technologies, INC. (Coralville, Iowa). Expected amplicon lengths were 238 bp and 273 bp for the A22893G and G30597A alleles, respectively.

EXAMPLE 9

Real-Time PCR Amplification

All reactions were carried out in a total volume of 25 μL. Reaction conditions were identical for A22893G and G30597A except where noted. Each reaction mixture contained 0.2 umol/l of each primer and a 1:12,500 dilution of SYBR™ Green I nucleic acid gel stain 10,000× in dimethyl sulfoxide (DMSO) (Molecular Probes); 0.2 mM of DATP, dCTP, dGTP, and dTTP; 1.0 U of Taq DNA polymerase (Promega, Madison, Wis.); 6% DMSO; and 20 to 120 ng of genomic DNA in 1× PCR buffer (pH 8.3, 10× solution containing 100 mM Tris-HCl, 500 mM KCl, 15 mM MgCl2 and 0.01% gelatin) (Sigma, St. Louis, Mo.).

The amplification program for both A22893G and G30597A consisted of 1 cycle of 95° C. with 120-second hold ("Hotstart") followed. by 30 cycles of 95° C. with 15-second hold, specified annealing temperature of 58° C. with 30-second hold, and 72° C. with 30-second hold. After amplification, melt analysis was performed by heating the reaction mixture from 60° C. to 95° C. at the rate of 0.2° C./s. A negative control without DNA template was run with every assay to assess the overall specificity.

EXAMPLE 10

PCR Product Analysis

PCR products were analyzed as described above. Genomic DNA obtained from individuals determined by sequencing to be homo-, hetero-, and nullizygous for the *3 allele were used to develop the CYP3A5*3 genotyping assay. The CYP3A5*6 allele has a frequency of approximately 6% in African-Americans, but the *6 allele was not found in Caucasians. Due to the low prevalence of the *6 allele, the inventors were unable to identify an individual with the *6/*6 genotype. Thus, genomic DNA obtained from individuals determined by sequencing to be hetero- and nullizygous for the *6 allele were used to develop the CYP3A5*6 genotyping assay.

EXAMPLE 11

Genotyping Results

Allele-specific primers containing an additional nucleotide mismatch at the third base from the 3' termini had little effect on specific PCR product yield. However, non-specific PCR product yield was drastically reduced to undetectable levels. Consequently, PCR conditions were optimized such that the threshold cycle (Ct) was exceeded only when specific amplification occurred (i.e., only in the presence of a primer: template match).

Figure 4A:
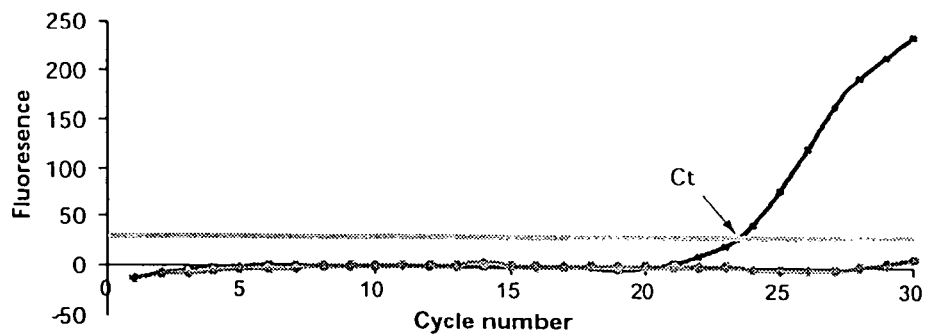
FIG. 4A–C: CYP3A5 allelic discrimination using human genomic DNA as template. Human genomic DNA obtained from individuals with *1/*1 (FIG. 4A), *3/*3 (FIG. 4B), or *1/*3 (FIG. 4C) genotype interrogated for the presence of either the *1 or *3 allele using wild-type (-♦-, blue) and mutant-specific (-♦-, orange) primers.
Figure 5A:
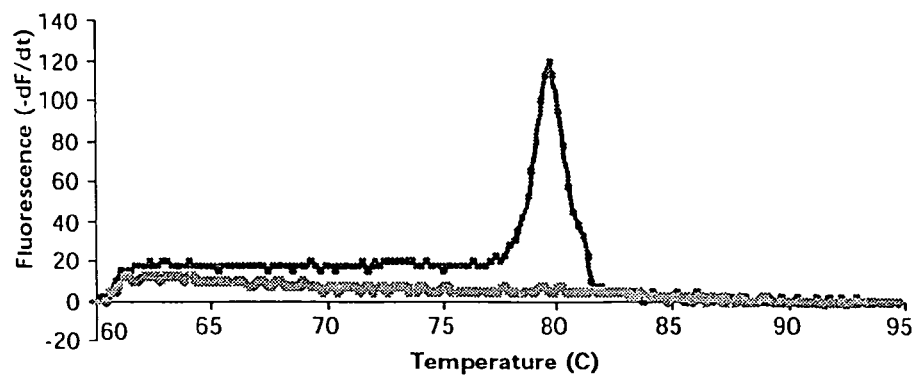
FIGS. 5A–C: Melting curve analysis of PCR products using SYBR™ Green I. Negative first derivative of fluorescence versus temperature curves for PCR products obtained after amplification of *1/*1 (FIG. 5A), *3/*3 (FIG. 5B), or *1/*3 (FIG. 5C) genomic DNA using wild-type (-♦-, blue) and mutant-specific (-♦-, orange) primers.

FIG. 4A illustrates the results of the CYP3A5*3 allelic discrimination assay using CYP3A5*1/*1 genomic DNA amplified with the common primer 3A5*3C and either the wild-type specific primer 3A5*3W or the mutant-specific primer 3A5*3M. When primers 3A5*3C and 3A5*3W were used to amplify *1/*1 genomic DNA, the PCR growth curve exceeded the Ct value of approximately 25 cycles (FIG. 4A), and the melting analysis (negative first derivative) yielded a characteristic sharp peak at approximately 80° C. for the product (FIG. 5A). PCR growth curves remained at approximately background fluorescence (FIG. 4A) when 3A5*3C and 3A5*3M were used to amplify *1/*1 genomic DNA and no distinct melting peaks were noted (FIGS. 4A and 5A).

Figure 4B:
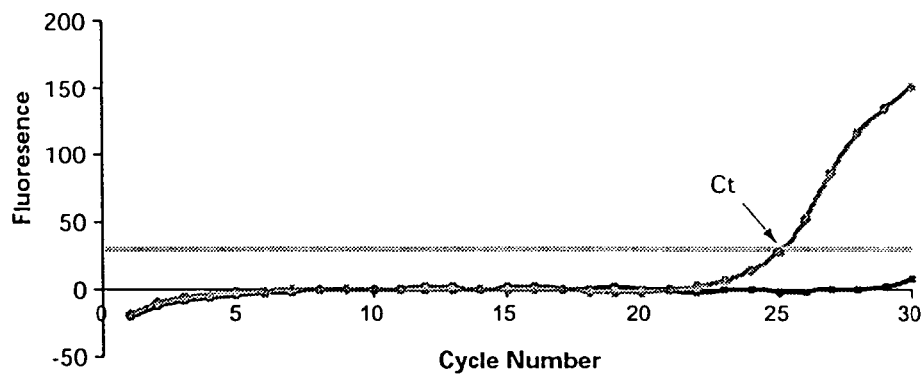
Figure 5B:
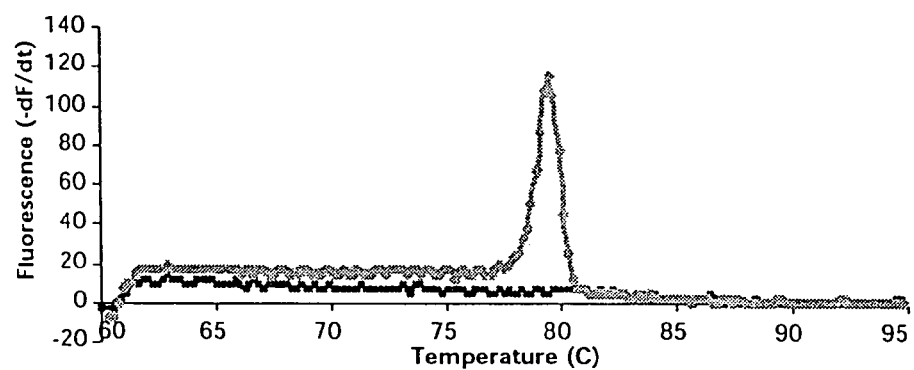

Agarose gel electrophoresis yielded the expected 238 bp fragment when *1/*1 DNA was amplified with primers 3A5*3C and 3A5*3W. However, no bands were visualized after *1/*1 genomic DNA was amplified using primers 3A5*3C and 3A5*3M (data not shown). Similarly, allelic discrimination was achieved after amplification of *3/*3 DNA using primers 3A5*3C, 3A5*3M, and 3A5*3W (FIGS. 4B and 5B).

Figure 4C:
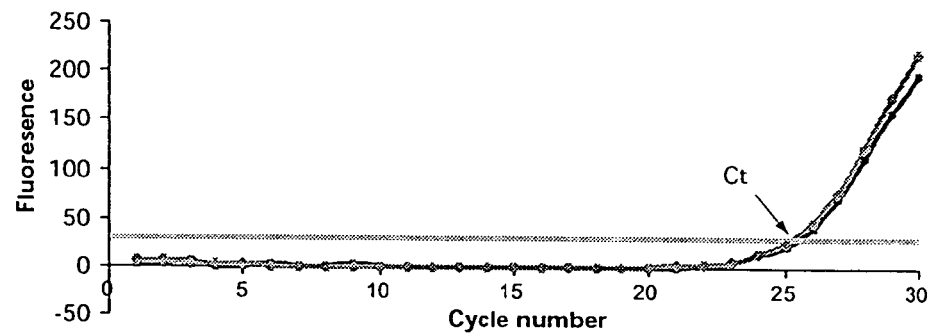
Figure 5C:
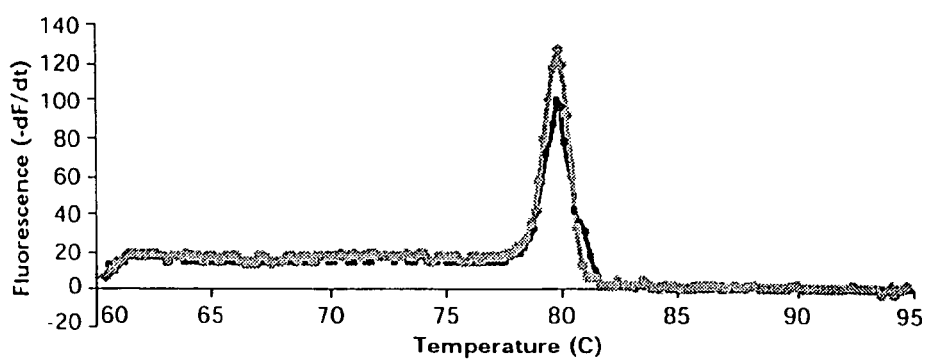

Overlapping PCR growth curves yielding similar Ct values were obtained when *1/*3 genomic DNA was amplified using wildtype and mutant-specific primers (FIG. 4C). In addition, a distinct melt analysis peak was present after amplification with both wild-type and mutant-specific primers (FIG. 5C). These results accurately predict the presence of both wild-type and mutant CYP3A5 alleles in the heterozygote control. Sequencing of genomic DNA and individual PCR products obtained from individuals homozygous, heterozygous, and nullizygous for *3 were in perfect agreement with real-time PCR assay results. Results obtained from optimization and application of the CYP3A5*6 genotyping assay to individuals nullizygous and heterozygous. for the *6 allele were similar to those reported for CYP3A5*3 (data not shown). Melt curve analysis yielded a characteristic sharp peak at approximately 77° C. (Table 2).

TABLE 2

Primer Sequences For CYP3A5*3 And CYP3A5*6 Genotyping

| Primer[a] | Sequence[b] | $T_m$[c] |
|---|---|---|
| CYP3A5*3 | | 80° C. |
| 3A5*3W | 5' 22912 TCCAAACAGGGAAGAGAAAT 3' 22893 (SEQ ID NO:11) | |
| 3A5*3M | 5' 22912 TCCAAACAGGGAAGAGAAC 3' 22893 (SEQ ID NO:12) | |
| 3A5*3C | 5' 22675 ACTGCCCTTGCAGCATTTAG 3' 22694 (SEQ ID NO:13) | |
| CYP3A5*6 | | 77° C. |
| 3A5*6W | 5' 30578 CCTTTGTGGAGAGCACTGAG 3' 30597 (SEQ ID NO:14) | |
| 3A5*6M | 5' 30578 CCTTTGTGGAGAGCACTGAA 3' 30597 (SEQ ID NO:15) | |
| 3A5*6C | 5' 30850 TGGTGGGGTGTTGACAGCTA 3' 30831 (SEQ ID NO:16) | |

[a]W indicates wild type specific primer; M, mutant-specific primer; C, common primer used in allelic discrimination assays.
[b]Nucleotides shown in bold indicate nucleotides mismatches from published wild type sequence (Genbank #AC005020).
[c]Amplicon melt temperature ($T_m$) obtained from melt curve analysis.

The following references were cited herein:

Bottema et al., Polymerase chain reaction amplification of specific alleles: a general method of detection of mutations, polymorphisms, and haplotypes. Methods Enzymol. 218: 388–402 (1993).

Kim et al., Identification of functionally variant MDR1 alleles among European Americans and African Americans. Clin. Pharmacol. Ther. 70:189–199 (2001).

Kuehl et al., Sequence diversity in CYP3A promoters and characterization of the genetic basis of polymorphic CYP3A5 expression. Nat. Genet. 27:383–91 (2001).

Newton et al., Analysis of any point mutation in DNA: the amplification refractory mutation system (ARMS). Nucleic Acids Res. 17:2503–2516 (1989).

Okimoto & Dodgson, Improved PCR amplification of multiple specific alleles (PAMSA) using internally mismatched primers. Biotechniques 21:20–26 (1996).

Sommer et al., PCR amplification of specific alleles (PASA) is a general method for rapidly detecting known single-base changes. Biotechniques 12:82–87 (1992).

Tang et al., Distinct haplotype profiles and strong linkage disequilibrium at the MDR1 multidrug transporter gene locus in three ethnic Asian populations. Pharmacogenetics 12:437–450 (2002).

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

What is claimed is:

1. A kit for genotyping human multidrug resistance gene (MDR1) single nucleotide polymorphism C3435T, comprising:
   a primer pair consisting of the primer sequences SEQ ID NO: 1 and SEQ ID NO: 3; and
   a primer pair consisting of the primer sequences SEQ ID NO: 2 and SEQ ID NO: 3.

2. A primer pair useful for genotyping human multidrug resistance gene (MDR1) single nucleotide polymorphism C3435T consisting of the primer sequences SEQ ID NO: 1 and SEQ ID NO: 3 or consisting of the primer sequences SEQ ID NO: 2 and SEQ ID NO: 3.

3. A method of genotyping human multidrug resistance gene (MDR1) single nucleotide polymorphism C3435T, comprising the steps of:
   preparing DNA samples from an individual;
   amplifying said DNA with a first primer pair comprising a wild type-specific primer and common reverse primer, wherein the first primer pair is a primer pair consisting of the primer sequences SEQ ID NO: 1 and SEQ ID NO: 3 and also amplifying said DNA with a second primer pair comprising a mutant-specific primer and common reverse primer, wherein the second primer pair is a primer pair consisting of the primer sequences SEQ ID NO: 2 and SEQ ID NO: 3 and
   identifying the products of said DNA amplification,
   wherein the presence of products amplified by said mutant-specific primer and said ieverse primer indicate said individual has at least one "T" allele at position 3435 of the MDR1 gene.

4. The method of claim 3, wherein said products of DNA amplification are identified by a method selected from the group consisting of real-time fluorescence-based analysis, melt curve analysis and gel electrophoresis.

* * * * *

SEQUENCE LISTING

<160> NUMBER OF SEQ ID NOS: 16

<210> SEQ ID NO 1
<211> LENGTH: 21
<212> TYPE: DNA
<213> ORGANISM: artificial sequence
<220> FEATURE:
<221> NAME/KEY: primer_bind
<223> OTHER INFORMATION: 3435W primer sequence for MDR1 genotyping

<400> SEQUENCE: 1
gtggtgtcac aggaagaggt c                                              21

<210> SEQ ID NO 2
<211> LENGTH: 21
<212> TYPE: DNA
<213> ORGANISM: artificial sequence
<220> FEATURE:
<221> NAME/KEY: primer_bind
<223> OTHER INFORMATION: 3435M primer sequence for MDR1 genotyping

<400> SEQUENCE: 2
gtggtgtcac aggaagaggt t                                              21

-continued

```
<210> SEQ ID NO 3
<211> LENGTH: 21
<212> TYPE: DNA
<213> ORGANISM: artificial sequence
<220> FEATURE:
<221> NAME/KEY: primer_bind
<223> OTHER INFORMATION: 3435R primer sequence for MDR1 genotyping

<400> SEQUENCE: 3
actataggcc agagaggctg c                                              21

<210> SEQ ID NO 4
<211> LENGTH: 21
<212> TYPE: DNA
<213> ORGANISM: artificial sequence
<220> FEATURE:
<221> NAME/KEY: primer_bind
<223> OTHER INFORMATION: 2677W primer sequence for MDR1 genotyping

<400> SEQUENCE: 4
agtttgactc accttccctg c                                              21

<210> SEQ ID NO 5
<211> LENGTH: 21
<212> TYPE: DNA
<213> ORGANISM: artificial sequence
<220> FEATURE:
<221> NAME/KEY: primer_bind
<223> OTHER INFORMATION: 2677M primer sequence for MDR1 genotyping

<400> SEQUENCE: 5
agtttgactc accttccctg a                                              21

<210> SEQ ID NO 6
<211> LENGTH: 21
<212> TYPE: DNA
<213> ORGANISM: artificial sequence
<220> FEATURE:
<221> NAME/KEY: primer_bind
<223> OTHER INFORMATION: 2677C primer sequence for MDR1 genotyping

<400> SEQUENCE: 6
gctataggtt ccaggcttgc t                                              21

<210> SEQ ID NO 7
<211> LENGTH: 21
<212> TYPE: DNA
<213> ORGANISM: artificial sequence
<220> FEATURE:
<221> NAME/KEY: primer_bind
<223> OTHER INFORMATION: sense primer for sequencing the
      G2677T locus

<400> SEQUENCE: 7
aagattgctt tgaggaatgg t                                              21

<210> SEQ ID NO 8
<211> LENGTH: 21
<212> TYPE: DNA
<213> ORGANISM: artificial sequence
<220> FEATURE:
<221> NAME/KEY: primer_bind
<223> OTHER INFORMATION: antisense primer for sequencing the
      G2677T locus

<400> SEQUENCE: 8
```

```
gctataggtt ccaggcttgc t                                           21
```

<210> SEQ ID NO 9
<211> LENGTH: 19
<212> TYPE: DNA
<213> ORGANISM: Artificial sequence
<220> FEATURE:
<221> NAME/KEY: primer_bind
<223> OTHER INFORMATION: sense primer for sequencing the
    C3435T locus

<400> SEQUENCE: 9

```
gagcccatcc tgttgactg                                              19
```

<210> SEQ ID NO 10
<211> LENGTH: 21
<212> TYPE: DNA
<213> ORGANISM: Artificial sequence
<220> FEATURE:
<221> NAME/KEY: primer_bind
<223> OTHER INFORMATION: antisense primer for sequencing the
    C3435T locus

<400> SEQUENCE: 10

```
actataggcc agagaggctg c                                           21
```

<210> SEQ ID NO 11
<211> LENGTH: 20
<212> TYPE: DNA
<213> ORGANISM: Artificial sequence
<220> FEATURE:
<221> NAME/KEY: primer_bind
<223> OTHER INFORMATION: 3A5*3W primer sequence for CYP3A5*3
    genotyping

<400> SEQUENCE: 11

```
tccaaacagg gaagagaaat                                             20
```

<210> SEQ ID NO 12
<211> LENGTH: 20
<212> TYPE: DNA
<213> ORGANISM: Artificial sequence
<220> FEATURE:
<221> NAME/KEY: primer_bind
<223> OTHER INFORMATION: 3A5*3M primer sequence for CYP3A5*3
    genotyping

<400> SEQUENCE: 12

```
tccaaacagg gaagagaaac                                             20
```

<210> SEQ ID NO 13
<211> LENGTH: 20
<212> TYPE: DNA
<213> ORGANISM: Artificial sequence
<220> FEATURE:
<221> NAME/KEY: primer_bind
<223> OTHER INFORMATION: 3A5*3C primer sequence for CYP3A5*3
    genotyping

<400> SEQUENCE: 13

```
actgcccttg cagcatttag                                             20
```

<210> SEQ ID NO 14
<211> LENGTH: 20
<212> TYPE: DNA
<213> ORGANISM: Artificial sequence
<220> FEATURE:
<221> NAME/KEY: primer_bind -continued
<223> OTHER INFORMATION: 3A5*6W primer sequence for CYP3A5*6
      genotyping

<400> SEQUENCE: 14
cctttgtgga gagcactgag                                                    20

<210> SEQ ID NO 15
<211> LENGTH: 20
<212> TYPE: DNA
<213> ORGANISM: Artificial sequence
<220> FEATURE:
<221> NAME/KEY: primer_bind
<223> OTHER INFORMATION: 3A5*6M primer sequence for CYP3A5*6
      genotyping

<400> SEQUENCE: 15
cctttgtgga gagcactgaa                                                    20

<210> SEQ ID NO 16
<211> LENGTH: 20
<212> TYPE: DNA
<213> ORGANISM: Artificial sequence
<220> FEATURE:
<221> NAME/KEY: primer_bind
<223> OTHER INFORMATION: 3A5*6C primer sequence for CYP3A5*6
      genotyping

<400> SEQUENCE: 16
tggtggggtg ttgacagcta                                                    20